US009205182B2

(12) United States Patent
Clement et al.

(10) Patent No.: US 9,205,182 B2
(45) Date of Patent: Dec. 8, 2015

(54) METHODS AND APPARATUS FOR REDUCING DELETERIOUS EFFECTS OF X-RAY RADIATION UPON IMPLANTABLE MEDICAL DEVICE CIRCUITRY

(75) Inventors: Wesley J. Clement, Andover, MN (US); Hiroshi Fujimoto, Fujisawa (JP); Jeffrey D. Wilkinson, Vadnais Heights, MN (US); John R. Buysman, Coon Rapids, MN (US); Girard B. Borgerding, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2540 days.

(21) Appl. No.: 11/096,801

(22) Filed: Mar. 31, 2005

(65) Prior Publication Data

US 2006/0241398 A1 Oct. 26, 2006

(51) Int. Cl.
*A61N 1/05* (2006.01)
*A61L 31/18* (2006.01)
*A61N 1/37* (2006.01)
*A61N 1/375* (2006.01)

(52) U.S. Cl.
CPC . *A61L 31/18* (2013.01); *A61N 1/37* (2013.01); *A61N 1/375* (2013.01); *A61N 1/3718* (2013.01)

(58) Field of Classification Search
CPC ... A61N 1/05; A61N 1/37223; A61N 1/3756; A61N 2001/086; A61B 5/0031; A61B 5/05
USPC .............. 600/1–3, 424–425; 607/115–119, 5, 607/36–38; 128/897, 899; 250/505.1–519.1; 257/659–660, 678, 257/730
See application file for complete search history.

(56) References Cited

U.S. PATENT DOCUMENTS

| | | | | |
|---|---|---|---|---|
| 3,918,460 | A | * 11/1975 | King et al. | 607/36 |
| 5,456,698 | A | 10/1995 | Byland et al. | |
| 5,749,910 | A | * 5/1998 | Brumwell et al. | 607/36 |
| 5,889,316 | A | * 3/1999 | Strobel et al. | 257/659 |

(Continued)

FOREIGN PATENT DOCUMENTS

| | | |
|---|---|---|
| EP | 1050321 A2 | 8/2000 |
| JP | 638598 | 7/2007 |

OTHER PUBLICATIONS

Edling, "DIXI—a Hybrid Pixel Detector for X-ray Imaging," Comprehensive Summaries of Uppsala Dissertations from the Facutly of Science and Technology, ACTA Universitatis Upsaliensis, Uppsala 2004, pp. 1-65.
Yamaji, "Influences of CT on a Pacemaker—Examination Using a Pacemaker Telemetry," Arrhythmia, vol. 20, No. 2, 2004, pp. 113-114.

(Continued)

*Primary Examiner* — Christine H Matthews
(74) *Attorney, Agent, or Firm* — Evans M. Mburu

(57) ABSTRACT

According to the invention methods and structures for determining whether impingement of x-ray radiation upon potentially vulnerable discrete components, circuits and/or circuit pathways of an implantable medical device (IMD) causes modifications or damage thereto. The invention includes structures for deflecting impingement of x-ray radiation from said potentially vulnerable components, circuits and/or circuit pathways. The x-ray radiation can be generated by various imaging modalities or unknown sources. Myriad IMDs can utilize the teaching of the present invention, including for example, a pacemaker, a drug delivery pump, a nerve stimulation device, a muscle stimulation device, an implantable cardioverter-defibrillator, a subcutaneous defibrillator, a deep brain stimulator or the like.

19 Claims, 15 Drawing Sheets

(56) References Cited

U.S. PATENT DOCUMENTS

| | | | |
|---|---|---|---|
| 5,982,631 A * | 11/1999 | Bowles et al. | 361/771 |
| 6,121,672 A | 9/2000 | Benedetto | |
| 7,127,294 B1 * | 10/2006 | Wang et al. | 607/36 |
| 2003/0004552 A1 * | 1/2003 | Plombon et al. | 607/27 |
| 2003/0025089 A1 | 2/2003 | Featherby et al. | |
| 2003/0088146 A1 | 5/2003 | Slater et al. | |
| 2003/0140931 A1 * | 7/2003 | Zeijlemaker et al. | 128/899 |
| 2004/0056334 A1 * | 3/2004 | Longden et al. | 257/660 |
| 2005/0004637 A1 | 1/2005 | Singhal et al. | |
| 2005/0033370 A1 * | 2/2005 | Jelen et al. | 607/36 |
| 2005/0137670 A1 * | 6/2005 | Christopherson et al. | 607/122 |

OTHER PUBLICATIONS

Sakai, "Effect of CT Scanning on a Pacemaker—Examination in Patients Implanted with a Pacemaker," Arrhythmia, vol. 20, No. 2, 2004, pp. 118-119.

Rodriguez, "Radiation-Induced Effects in Multiprogrammable Pacemakers and Implantable Defibrillators," PACE, vol. 14, Dec. 1991, pp. 2143-2153.

Lewin, "Radiation Induced Failures of Complementary Metal Oxide Semiconductor Containing Pacemakers: A Potentially Lethal Complication," J. Radiation Ocology Biol. Phys, vol. 10, pp. 1967-1969.

Marbach, "Management of Radiation Oncology Patients with Implanted Cardiac Pacemakers: Report of AAPM Task Group No. 34," Med Phys, 21 (1), Jan. 1994, pp. 85-90.

* cited by examiner

METHODS AND APPARATUS FOR REDUCING DELETERIOUS EFFECTS OF X-RAY RADIATION UPON IMPLANTABLE MEDICAL DEVICE CIRCUITRY

CROSS REFERENCE TO RELATED APPLICATION

The present patent document is related to co-pending non-provisional U.S. patent application Ser. No. 11/096,671 entitled, "METHODS AND APPARATUS FOR REDUCING SPURIOUS SIGNALS IN IMPLANTABLE MEDICAL DEVICES CAUSED BY X-RAY RADIATION," filed on even date herewith; the contents of which are hereby incorporated by reference.

FIELD OF THE INVENTION

This invention relates generally to implantable medical devices (IMDs) and, more particularly, to a method and apparatus for reducing negative effects of x-ray radiation impinging upon operative circuitry of active IMDs (e.g., pacemakers, nerve stimulators, therapeutic-substance pumps, physiologic monitors, etc.); in particular, the invention relates to reducing such x-ray radiation impingement during positron emission tomography (PET), computed tomography (CT), fluoroscopy-type and other x-ray imaging scans including newer imaging modalities such as digital subtraction angiography (DSA) and Angio-CT as well an incident x-ray radiation impingement from unknown sources.

DESCRIPTION OF THE RELATED ART

Since the introduction of implantable pacemakers in the 1960s, there have been considerable advances in both the fields of electronics and medicine, such that there is presently a wide assortment of commercially available body-implantable electronic medical devices. The class of IMDs now includes pacemakers, implantable cardioverter-defibrillator (ICDs), defibrillators, neural stimulators, and drug administering devices, among others. Today's state-of-the-art IMDs are vastly more sophisticated and complex than earlier ones, and are capable of performing significantly more complex tasks. Additionally, the therapeutic benefits of such devices have been well proven.

As the functional sophistication and complexity of IMDs have increased over the years, however, they have also been found to be vulnerable to more sophisticated and complex sources of interference. In particular, conventional IMDs have been found to be vulnerable to electromagnetic interference signals produced for example by magnetic resonance imaging (MRI) devices during a magnetic resonance imaging (MRI) scanning session. For example, co-pending application Ser. No. 10/004,237 by Yong K. Cho et al. addresses this type of vulnerability by using mechanically-based cardiac activity monitoring systems in lieu of typical electrically-based sensing systems when an IMD is exposed to supra-threshold MRI radiation. The Cho et al. application was filed 31 Oct. 2001 and is entitled, "ALTERNATIVE SENSING METHOD FOR IMPLANTABLE MEDICAL DEVICE IN MAGNETIC RESONANCE IMAGING DEVICE," the contents of which are hereby incorporated by reference herein.

Conventional cardiac IMDs typically use intra-cardiac electrograms (EGMs) for cardiac rhythm sensing and rely upon precisely measured and timed intervals to reliably deliver a desired therapy. The inventors have discovered that x-ray radiation exposure can negatively affect both the sensing amplifiers (causing so-called over-sensing), the amplifiers used to collect EGMs, the clock monitor circuitry used in the crystal oscillator circuit (used to generate the main timing-clock for certain IMDs) among other components and circuits. Furthermore, other components or circuits that can be negatively affected include battery status monitors, impedance measuring amplifiers, activity sensor amplifier and the like.

That is, during exposure to x-ray radiation for example during a CT-scanning session or a fluoroscopy-imaged examination, the collected cardiac EGMs may become distorted due to over-sensing and/or modified due to an incorrect clock performance so that an accurate assessment of the cardiac rhythm and/or function becomes more difficult. In addition, in certain IMDs a full and/or a partial electrical reset (PER) can occur which inevitably temporarily reduces therapy delivery.

The following passage is credited to Fredrik Edling's dissertation of 15 Oct. 2004 entitled, "DIXI—a Hybrid Pixel Detector for X-Ray Imaging" which was published in the *Uppsala Dissertations from the Faculty of Science and Technology* of Uppsala University (Sweden). Several modalities are used in radiology to image the human body. The focus in this thesis is put on planar projective X-ray imaging. Other ionizing modalities are for example computed tomography (CT), positron emission tomography (PET), nuclear medicine and three-dimensional angiography. Non-ionizing modalities are for example ultrasound and magnetic resonance imaging (MRI). These will not be discussed here, although it can be noted that the modalities are complementary. For example, PET gives a functional image of the body, while MRI is good at imaging soft tissue. Planar projective x-ray imaging is what we normally think of as x-ray imaging. The x-ray tube is positioned on one side of the patient, usually above and the imaging plate is positioned underneath the patient. The x-ray photon beam passes through the body and the acquired x-ray image is an inverted map of the attenuation in the body. For example, bone attenuates the x-ray photon flux to a greater extent than soft tissue. Photons are not only absorbed in the body, but they are also scattered. These scattered photons will, if not removed, decrease the signal-to-noise ratio in the image. The exposure has therefore to be increased, to obtain an equivalent contrast, compared to the case of no scattered photons. Methods used to remove the scattered photons include air-gaps and grids. Common to both is that they nevertheless increase the dose to the patient and it is therefore desirable to find other methods to discriminate the scattered photons. The photons interact with matter through the photoelectric effect, Compton scattering and pair production. In the photoelectric effect the photon is absorbed by an electron bound inside an atom. The electron is subsequently absorbed in the material. The vacancy in the electron shell is filled with an electron from an outer shell and in this transition a characteristic X-ray is emitted. The cross-section exhibits steps at the points where the different atomic shell energies are located. At energies above a shell energy, the electrons of that shell are no longer available for interactions and the cross-section subsequently drops. In Compton scattering the photon interacts with atomic electrons and loses part of it energy and changes direction on its way through matter. Besides Compton scattering resides the two cases of Rayleigh and Thomson scattering. These are classical processes and for the energies of interest for X-ray imaging their influences are very small and can mostly be neglected. The threshold energy for pair production is 1.022 MeV, which is far above the energies used in X-ray imaging.

The present invention is directed to eliminating, if not at least reducing, the possibly negative effects of x-rays impinging upon operative circuitry of IMDs.

SUMMARY OF THE INVENTION

In one aspect of the present invention, methods of fabricating an IMD having selective x-ray impervious shielding are provided. These methods include identifying one or more components, circuits and/or circuit paths that are potentially vulnerable to x-ray radiation and then coupling one or more x-ray radiation shields to potentially vulnerable circuitry operatively coupled of an IMD. In one form of the invention one or more shield members having at least one radiation-admitting aperture selectively allows radiation from an x-ray source to impinge upon circuitry or the like disposed below the aperture. During and/or following x-ray exposure the exposed circuitry is operated to determine whether the x-ray radiation modified or damaged any parts thereof. If modification or damage is confirmed then the location of the aperture is used to guide installation of radiation opaque material (e.g., a plate or portion of lead, relatively thicker region of IMD housing, a layer of material disposed to overlay a part of an integrated circuit or integrated circuit packaging, etc.). Of course, the final orientation of the IMD should be considered since as will be described and depicted, x-ray radiation attenuates when it travels through a body. Thus, the shield should be located on the interior of an IMD between the outer cover and the vulnerable circuitry. If the radiation opaque material is not biocompatible (e.g., lead) then the material must be installed within the interior of the IMD housing. Due to the ever decreasing volume and weight of current IMDs, the size and weight of the radiation material needs to be considered as well. Due to the foregoing the inventors have discovered that a lead plate having a relatively small surface area, if properly located within the IMD housing, can essentially eliminate x-ray radiation from impinging upon possibly vulnerable circuitry operatively coupled therein.

The inventors believe that they have discovered that the negative interaction(s) of x-ray radiation upon certain IMDs arises not from electrical and/or magnetic interference (perhaps somehow induced by the x-ray radiation) but rather from photoelectric or photo-current effects in combination from the phenomenon known as Compton scattering due to x-rays impinging upon insulating or semi-conductive materials (e.g., electrical circuitry, insulation, dielectric layers and/or conductors) disposed in and about an IMD.

The inventors applied standard planar, or essentially linear-static, x-ray sources, three-dimensional (3D) x-ray sources including fluoroscope-type, and CT-type "dynamically rotatable" x-ray sources and designed and tested prophylactic x-ray radiation shielding. The prophylactic x-ray radiation shielding for IMD circuitry, methods of fabrication of IMDs having said shielding and other aspects of the present invention are fully described, depicted and claimed hereinbelow. Those of skill in the art will certainly contemplate insubstantial modifications and applications once exposed to the teaching of the inventors provided herein and all such modifications and applications are expressly covered hereby.

Another aspect of the invention includes x-ray sensing capability so that a threshold-based response can be initiated (e.g., pacing mode switch to asynchronous pacing, implementation of a mechanical-based sensing regimen, or the like). In a related embodiment, upon detection of even a modicum of x-ray radiation a similar response occurs.

Electronic circuit components incorporate insulators, semi-conductors, and conductors in the form of very thin layers. The insulating layers separate conductor layers and prevent electrical currents (electrons) from flowing between the layers. The semi-conductors control currents between the conductors. When x-rays strike atoms in the insulating or semi-conducting materials, the x-rays displace electrons, creating "free" electrons in the materials. This is a combination of the photoelectric effect and Compton scattering, both well established physical phenomena. In the insulating layers, the free electrons allow small currents to flow between conducting layers. In the semi-conductors, the free electrons alter the control of currents. These changes in currents also cause small changes in the circuit voltages.

Certain pacemaker circuits, such as sense amplifiers and voltage monitors, have the function of measuring small voltage changes. These circuits can sometimes detect the small radiation-induced voltage changes, which may be reflected as oversensing by the device.

Certain IMDs manufactured by Medtronic, Inc. include a monitor circuit block that is used to verify continuous operation of the device clock. The intent of the circuit is to continuously monitor the clock. If anomalous operation of the clock is detected, the crystal oscillator reverts to a startup mode and a partial electrical reset (PER) is generated. Radiation induced photocurrents can cause the clock monitor circuit to operate incorrectly. When the high dose rate radiation is present, the clock monitor circuit forces the crystal oscillator into the startup mode and a PER is generated. Although the clock that is generated by the crystal oscillator operates normally during the radiation exposure, the monitor circuit operates incorrectly, and so may generate a PER.

BRIEF DESCRIPTION OF THE DRAWINGS

The invention may be understood by reference to the following description taken in conjunction with the accompanying drawings which are not rendered to scale, and in which like components are denoted by common reference numerals.

Figure 1:
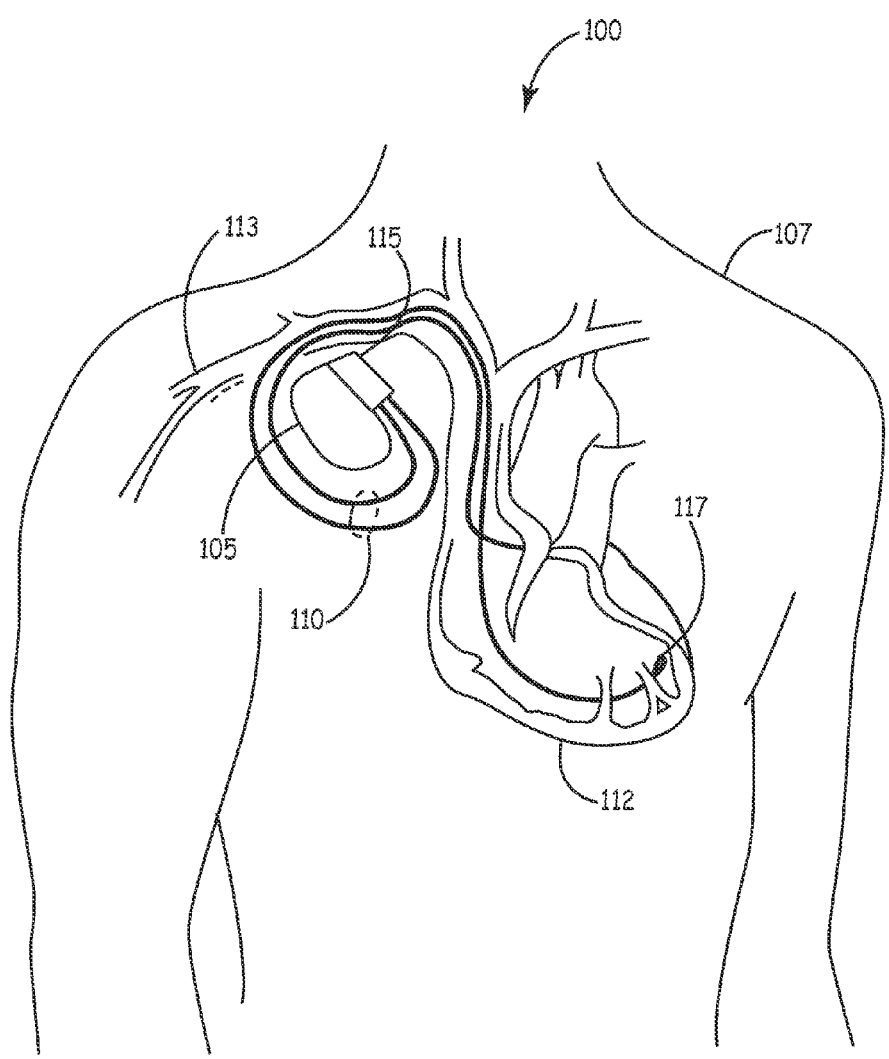
FIG. 1 schematically illustrates an IMD, in the form of a pacemaker, according to one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning now to the drawings, and specifically referring to FIG. 1, an IMD (IMD) system 100 is shown in accordance with one embodiment of the present invention. The IMD system 100 includes an IMD 105 that has been implanted in a patient 107. In accordance with the illustrated embodiment of the present invention, the implantable device 105 takes the form of a pacemaker for regulating the patient's heart rhythm. Although the implantable device 105 will be discussed in the form of a pacemaker, it will be appreciated that the implantable device 105 may alternatively take the form of a cardioverter, defibrillator, neural stimulator, drug administering device and the like without departing from the spirit and scope of the present invention.

The implantable device 105 is housed within a hermetically sealed, biologically inert outer housing or container, which may itself be conductive so as to serve as an electrode in the pacemaker's pacing/sensing circuit. One or more pacemaker leads, which are collectively identified by reference numeral 110, are electrically coupled to the implantable device 105 and extend into the patient's heart 112 through a cardiac vessel 113, such as a vein. The leads 110 are coupled to the IMD 105 via a connector block assembly 115. Disposed generally near a distal end of the leads 110 are one or more exposed conductive electrodes 117 for sensing cardiac activity and/or delivering electrical pacing stimuli (i.e., therapeutic signals) to the heart 112. The leads 110 may be implanted with their distal end situated adjacent the atrium or the ventricle, or both, of the heart 112.

Figure 2:
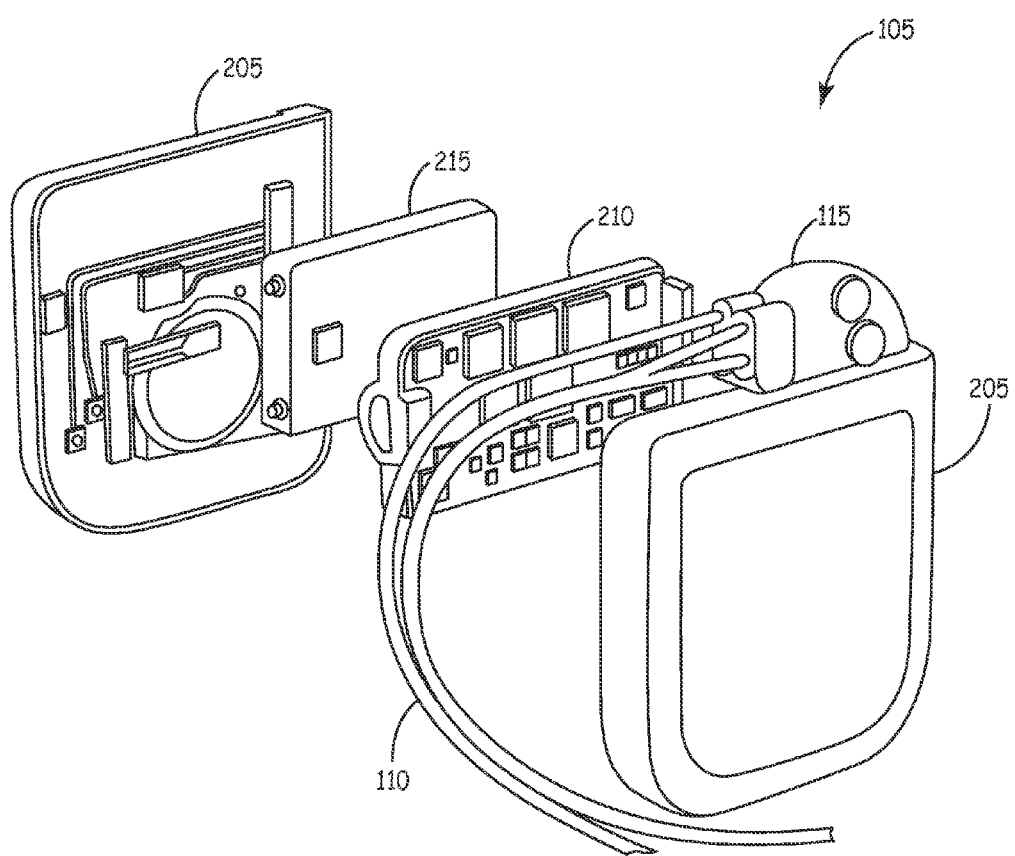
FIG. 2 schematically illustrates a three-dimensional, exploded view of the IMD of FIG. 1.

Turning now to FIG. 2, a three-dimensional, exploded view of the IMD 105 is shown in accordance with one embodiment of the present invention. The implantable device 105 is contained within a hermetically sealed, biologically inert housing 205 to protect the implantable device 105 from body fluids within the patient's body 107 in which the device 105 has been surgically implanted.

In the illustrated embodiment, the housing 205 includes a processor unit 210 and a battery 215. It will be appreciated that various other components may be included within the housing 205 of the implantable device 105 without departing from the spirit and scope of the present invention. In accordance with the illustrated embodiment, the processor unit 210 is configured to record diagnostic signals received via the conductive electrodes 117 located at the distal end of the leads 110, such as electric cardiac signals from the patient's heart 112. In response to the diagnostic signals received, the processor unit 210 may be configured to administer therapeutic signals to the patient's heart by directing electric pacing stimuli along the leads 110 to the patient's heart 112.

During the implantable device's relatively lengthy exposure to the higher-level of x-ray radiation, the patient's heart rate may increase; although, the implantable device 105 may not be able to detect this increase of the patient's heart rate due to the of x-ray radiation exposure. If the actual spontaneous heart rate of the patient 107 surpasses the IMD's stimulation rate during its exposure to the higher-level of x-ray radiation, then a condition known as "parasystoly" results, where the patient's actual spontaneous heart rhythm is at a higher rate than the stimulated rhythm produced by the implantable device 105. For example, if the patient's heart has a spontaneous rate of 95 ppm (beats per minute), and the implantable device 105 is attempting to stimulate the heart at 85 ppm, then parasystoly results. Parasystoly is a highly undesirable condition in that it will interfere with the patient's spontaneous rhythm, thereby potentially causing serious harm to the patient.

Figure 3:
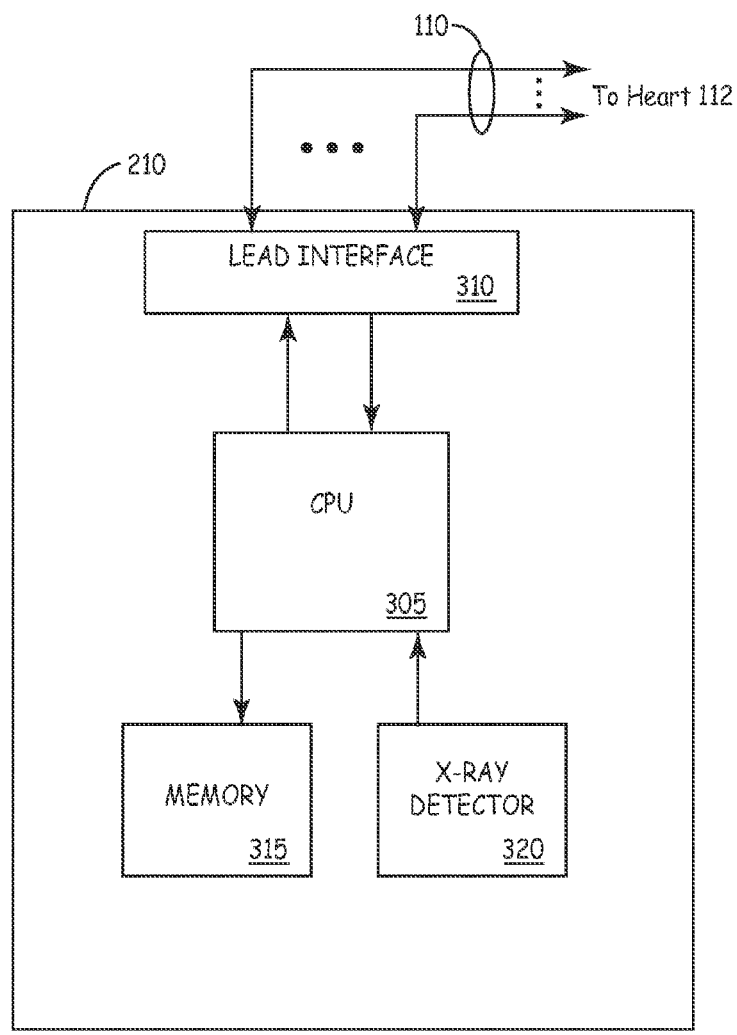
FIG. 3 schematically illustrates a block diagram of a processor unit of the IMD of FIG. 1 in accordance with one embodiment of the present invention.

Turning now to FIG. 3, a simplified block diagram of the processor unit 210 within the implantable device 105 is illustrated in accordance with one embodiment of the present invention. In one of its most simplistic forms, the processor unit 210 comprises a central processing unit (CPU) 305 for controlling the overall operation of the implantable device 105, and a lead interface 310 for coupling signals transmitted via the leads 110 between the electrodes 117 implanted within the patient's heart 112 and the implantable device 105. In accordance with the illustrated embodiment, these signals via the lead interface 310 may include electric cardiac signals sensed by the electrodes 117 implanted within the heart 112 that provide the CPU 305 with information regarding a spontaneous heart rate of the patient 107. The signals transmitted to the electrodes 117 via the leads 110 from the lead interface 310 may include electric pacing stimuli to stimulate the patient's heart based upon the CPU 305's evaluation of the patient's spontaneous or stimulated heart rate.

The processing unit 210 is further provided with a memory 315 for storing information related to the patient's spontaneous heart rate and the stimulated heart rate as determined by the CPU 305. In accordance with one embodiment, the spontaneous and stimulated heart rates may be stored over periodic intervals, thereby providing a history of the patient's spontaneous and stimulated heart rates. According to the illustrated embodiment, the memory 315, in addition to storing the aforementioned heart rate data, may also store program software for control of the CPU 305.

Figure 4:
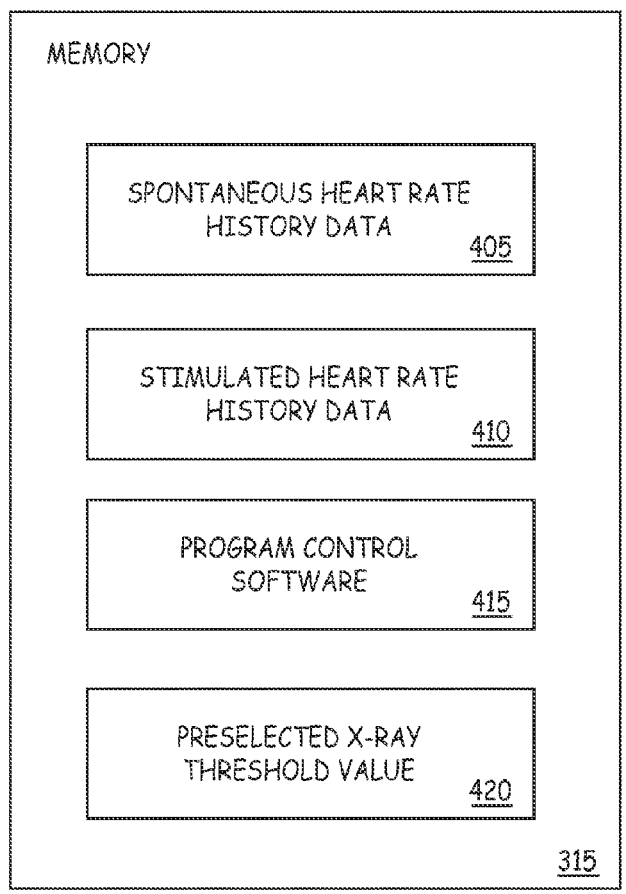
FIG. 4 provides a more detailed representation of a memory of the processor unit of FIG. 3.

Referring to FIG. 4, a more detailed representation of the memory 315 is shown according to the illustrated embodiment. The memory 315 includes a storage area 405 for storing the patient's spontaneous heart rate history data as sensed via the electrodes 117 implanted within the patient's heart 112. A storage area 410 of the memory 315 stores a stimulated heart rate history that indicates the rates at which the implantable device 105 stimulates the patient's heart 112 via electric pacing stimuli delivered through the electrodes implanted within the patient's heart. The memory 315 further includes a storage area 415 for storing software to control the processor unit 210 and a storage area 420 for storing a pre-selected of x-ray radiation threshold, which will be described in more detail as this description proceeds. It will be appreciated that the memory 315 may store various other data either in addition to or in lieu of the examples provided above without departing from the spirit and scope of the present invention. Furthermore, it will be appreciated that the data and/or software of the memory 315 may be programmed into or retrieved from their respective storage areas 405-420 utilizing conventional remote programming and/or data gathering techniques via radio frequency (RF) signals, for example.

Referring again to FIG. 3, the processing unit 210 comprises a of x-ray radiation detector 320, which detects the presence and strength of a of x-ray radiation experienced by the implantable device 105. In one embodiment, the x-ray radiation detector 320 takes the form of a three-dimensional Hall detector. It will be appreciated, however, that the detector 320 may alternatively take the form of various other of x-ray radiation detectors that detect the presence of a of x-ray radiation and indicate the strength of the field without departing from the spirit and scope of the present invention. In addition, the specific process by which the x-ray radiation detector 320 detects the presence of x-ray radiation (and its relative strength) is provided in U.S. Pat. No. 6,379,986 entitled "Method of Forming Tunnel Oxide Film for Superconducting X-ray Sensor Element," by Suzuki et al., the entire contents of which is incorporated herein by reference. According to Suzuki et al., in order to use as an X-ray sensor element, more aluminum is vapor deposited as an upper electrode. In this embodiment, a barrier oxidation coating having very good insulation properties is formed, and a converged oxygen ion beam is used using an oxygen ion gun of a secondary ion mass spectrometer, which means that formation of a tunnel junction region surrounding the circumference at the insulating film, and production of a tunnel oxidation film can be carried out at the same time. According to the present invention, after anodizing of a surface of a bulk aluminum material, a high quality tunnel oxidation film is produced by irradiation of oxygen ions, which means that it is possible to use a bulk aluminum material as an X-ray absorber of a sensor element, and it is possible to obtain an X-ray sensor element having high detection efficiency.

Accordingly, the specific techniques employed for of x-ray radiation detection and ascertaining the strength of the detected of x-ray radiation are not disclosed herein to avoid unnecessarily obscuring of the present invention.

In accordance with one embodiment of the present invention, when the x-ray radiation detector 320 determines the presence of x-ray radiation, a signal indicative of the strength of the x-ray radiation is sent from the detector 320 to the CPU 305. In the illustrated embodiment, when the x-ray radiation detector 320 detects the mere presence of x-ray radiation, a first (level 1) pre-selected x-ray radiation threshold is exceeded, and indicates that the implantable device 105 is within the presence of at least a modicum of x-ray radiation.

Subsequent to detecting the presence of the of x-ray radiation (and, thus exceeding a first, level 1 pre-selected of x-ray radiation threshold), the CPU 305 determines whether the strength of the detected x-ray radiation exceeds a second (level 2) pre-selected x-ray radiation threshold value. In the illustrated embodiment, the second (level 2) pre-selected threshold value is greater than the first (level 1) pre-selected x-ray radiation threshold and, may be selected so as to indicate the presence of a relatively strong x-ray radiation that may be produced by an x-ray imaging apparatus, for example. The second (level 2) pre-selected x-ray radiation threshold value may be stored within the memory 315 of the processor unit 210 for comparison by the CPU 305 with the strength of the detected x-ray radiation by the x-ray radiation detector 320. The storage area 420 (illustrated in FIG. 4) of the memory 315 may store the second (level 2) pre-selected x-ray radiation threshold value, which may be remotely modified (as previously discussed).

In accordance with the illustrated embodiment, if the strength of the detected x-ray radiation does not exceed the second (level 2) pre-selected x-ray radiation threshold, the implantable device 105 is disposed in the "magnet mode" of operation, and the implantable device 105 stimulates the patient's heart at a fixed stimulation rate, such as 85 ppm (pulses per minute), for example.

If, however, the CPU 305 determines that the strength of the x-ray radiation detected by the x-ray radiation detector 320 exceeds the second (level 2) pre-selected x-ray radiation threshold that is stored in the memory 315, the CPU 305 retrieves the last spontaneous or stimulated heart rate stored in the memory 315 prior to detecting the x-ray radiation by the detector 320. Upon receiving the last spontaneous or stimulated heart rate from the memory 315, the CPU 305 will then take this last heart rate, increment it by a predetermined incremental factor and make the result the new stimulation rate of the implantable device 105. In accordance with one embodiment, the predetermined incremental factor may be a ten percent increase of the last spontaneous or stimulated heart rate that was retrieved from the memory 315. Accordingly, if the last spontaneous or stimulated heart rate was 80 pm for the patient 107 prior to the detection of the presence of the x-ray radiation, the CPU 305 may stimulate the heart to a rate of 88 ppm (i.e., 8 ppm higher or 10% higher than the patient's heart rate prior to the x-ray radiation being detected). It will be appreciated, however, that the predetermined incremental factor may be a higher or lower percentage of the previously stored spontaneous or stimulated heart rate. It will further be appreciated that the predetermined incremental factor, as opposed to being a function of the patient's stored spontaneous or stimulated heart rate, may be a fixed value, such as 10 ppm, for example, that is added to the last stored spontaneous or stimulated heart rate. Of course, it will be appreciated that the fixed value may be higher or lower than the example provided.

In another embodiment of the present invention, a maximum stimulation rate (e.g., 120 ppm) can be imposed by the CPU 305. Accordingly, if the last recorded spontaneous or stimulated heart rate of the patient 107 with the addition of the predetermined incremental factor would exceed a stimulation rate of 120 ppm, the CPU 305 of the implantable device 105 may be configured to maintain a maximum stimulation rate of 120 ppm so as not to exceed a stimulated heart rate that may be deemed unsafe to the patient 107. It will be appreciated that the maximum stimulation rate set by the implantable device 105 may be higher or lower than 120 ppm without departing from the spirit and scope of the present invention. It will further be appreciated that the CPU 305 may further be configured to set a lower or minimum limit on the stimulation rate either in addition to or in lieu of the maximum stimulation rate (discussed above) without departing from the spirit and scope of the present invention. In one embodiment, the maximum and/or minimum allowable stimulation rates may be stored in the memory 315.

In one embodiment of the present invention, the CPU 305 will keep the stimulation rate augmented by the predetermined incremental factor until the CPU 305 determines that the detected x-ray radiation by the detector 320 is no longer present. Accordingly, while the implantable device 105 will be unable to detect possible spontaneous heart activity of the patient 107 during the x-ray radiation exposure, any small incremental increase in the stimulation rate during the x-ray radiation exposure will significantly reduce the likelihood of a parasystoly condition occurring. That is, because the implantable device 105 is provided with a new stimulation rate (i.e., the last spontaneous or stimulated heart rate has been increased by the predetermined incremental factor) for the duration of the stronger x-ray radiation exposure, any potential increase in the patient's heart rate during this exposure (which will be undetectable by the implantable device 105) will likely be lower than the new stimulation rate, thus substantially preventing parasystoly from occurring.

Figure 5:
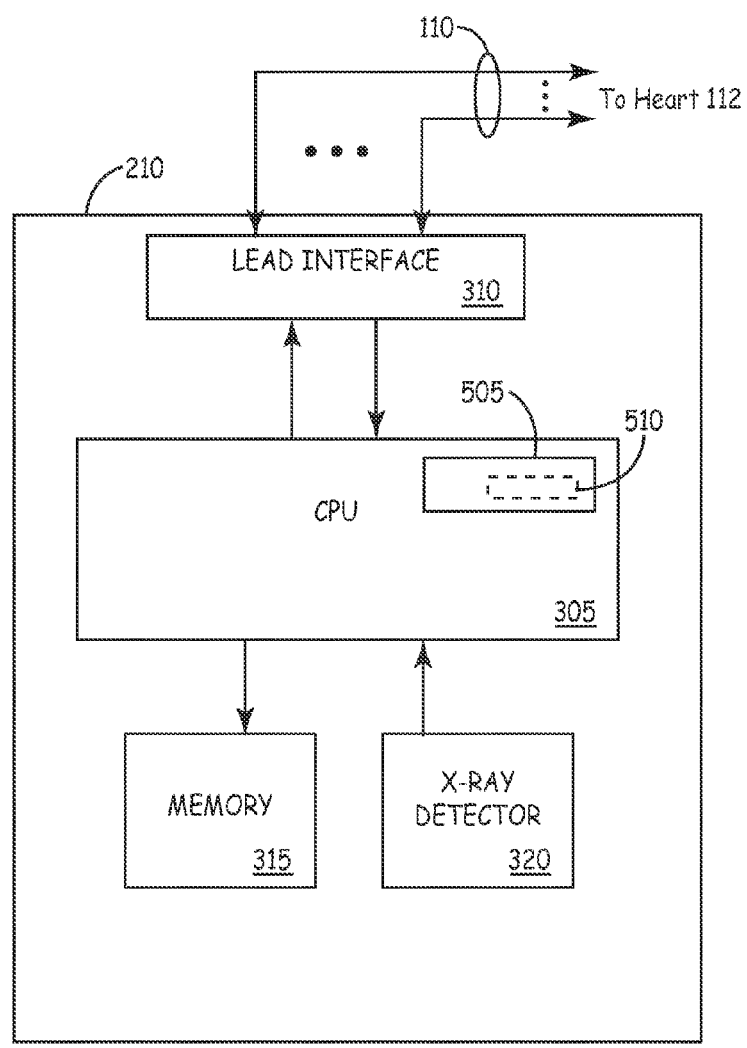
FIG. 5 schematically illustrates a block diagram of the processor unit of the IMD of FIG. 1 in accordance with another embodiment of the present invention.

Turning now to FIG. 5, the processor unit 210 of the IMD 105 depicts another embodiment of the present invention. In this particular embodiment, the IMD 105 may be alternatively configured to detect the presence of x-ray radiation interference signals and/or fabricated to reduce the possibility of impingement of x-ray radiation upon certain circuitry 510 of the IMD 105. The detection of the x-ray radiation may be accomplished via an HF radiation detector 320 as previously described. The CPU 305 may be configured to provide the IMD 105 with a new stimulation rate (which is the last stored spontaneous or stimulated rate increased by the predetermined incremental factor, as previously discussed) in response to the strength of the detected x-ray radiation signals exceeding a pre-selected threshold value. The pre-selected radiation threshold value may, in one embodiment, be stored in the memory 315 for comparison with the strength of the detected radiation that are detected by the radiation detector 320. It will also be appreciated that an x-ray impervious material (e.g., lead plate(s) 505) may either be used in lieu of x-ray radiation detector 320 or may be used in addition to the of x-ray radiation detector 320 (as depicted in FIG. 5).

Figure 6:
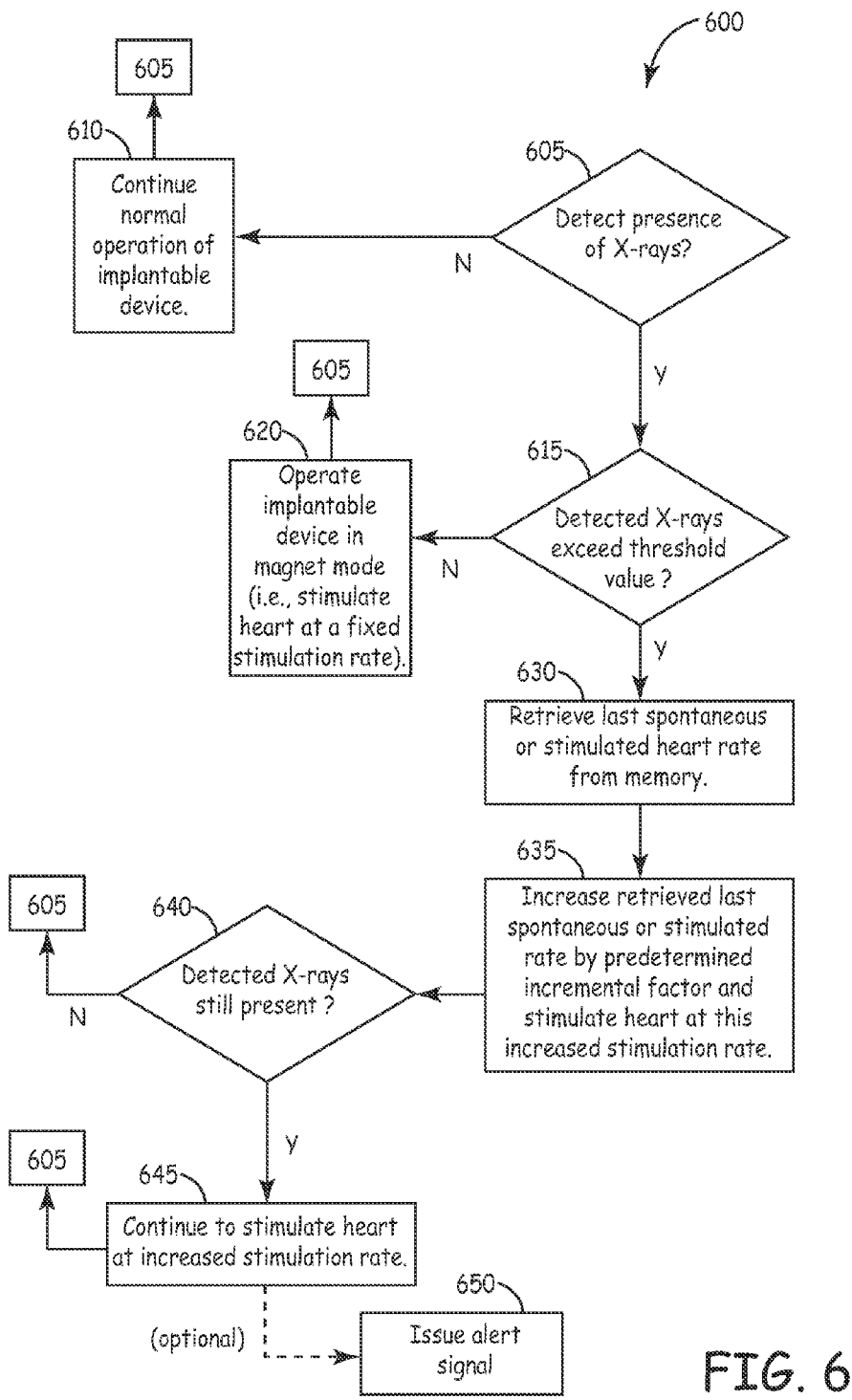
FIG. 6 illustrates a process for controlling the IMD of FIG. 1 in response to the presence of a strong of x-ray radiation according to one embodiment of the present invention.

Turning now to FIG. 6, a process 600 is illustrated for controlling the IMD 105 in response to the detection of relatively strong x-ray radiation impinging upon an x-ray detector (320) operatively coupled to circuitry disposed in the interior of a biocompatible enclosure for the IMD 105. In this embodiment the x-ray detector includes variable threshold capability so that one or more preset or adjustable x-ray detection regimes can be utilized. The process 600 commences at block 605 where the of x-ray radiation detector 320 of the processor unit 120 determines the presence of a of x-ray radiation within the implantable device 105. If the x-ray radiation detector 320 does not determine the presence of a of x-ray radiation in block 605, the implantable device 105 continues its normal operation at block 610 until the detector 320 detects the presence of x-ray radiation at block 605.

If the x-ray radiation detector 320 detects the presence of x-ray radiation at block 605 so as to indicate that a first (level 1) pre-selected x-ray radiation threshold has been exceeded, the process 600 continues to block 615, where the CPU 305 determines if the strength of the detected x-ray radiation by the x-ray radiation detector 320 exceeds a second (level 2) pre-selected x-ray radiation threshold value. In one embodiment, the second (level 2) pre-selected x-ray radiation threshold value may be stored in the memory 315 (as shown in FIG. 4) of the processing unit 210 for comparison by the CPU 305 to the strength of the detected x-ray radiation by the field detector 320. If the strength of the detected x-ray radiation is lower than the second (level 2) pre-selected x-ray radiation threshold value stored in the memory 315, the process 600 proceeds to block 620 where the implantable device 105 may enter into a "magnet mode" of operation where the implantable device 105 will stimulate the patient's heart at a fixed stimulation rate (e.g., 85 ppm) that is irrespective of the patient's actual intrinsic rhythm. Subsequent to being disposed in the "magnet mode," at block 620, the process reverts back to block 605, where the x-ray radiation detector 320 determines if the of x-ray radiation is still present.

If the detected x-ray radiation by the detector 320 exceeds the second (level 2) pre-selected x-ray radiation threshold value at block 615 (i.e., a relatively strong x-ray radiation is detected), then the process 600 proceeds to block 630 where the CPU 305 recalls the last spontaneous or stimulated heart rate stored in the memory 315 prior to the pre-selected x-ray radiation threshold being exceeded. At block 635, the CPU 305 then augments this recalled last heart rate, be it spontaneous or stimulated, of the implantable device 105 by a predetermined incremental factor, which may be a function of the spontaneous or stimulated heart rate retrieved from the memory 315 at block 630, and stimulates the heart 112 at this augmented stimulation rate. In accordance with the illustrated embodiment, the predetermined incremental factor may be a percentage of the stored spontaneous or stimulated rate, such as 10%, for example. It will further be appreciated that the predetermined incremental factor may be a fixed value of 10 ppm, for example, to be added to the last retrieved spontaneous or stimulated heart rate to then become the new stimulation rate of the implantable device 105.

The process 600 proceeds to block 640 where it is determined if the detected x-ray radiation is still present. If the detected x-ray radiation is no longer present, the process reverts back to block 605. If, however, the previously detected x-ray radiation is still present, then the CPU 305 (at block 645) continues to stimulate the patient's heart at the new augmented stimulation rate until it is determined that the of x-ray radiation is no longer present and, optionally, an alert signal is issued (at block 650). The alert signal 650 can include a signal originating from the IMD 105 such as vibratory motion, audible sounds or the like. In addition or in lieu of the foregoing, the IMD 105 can provide wireless communication to a remote IMD programming station and/or reach a clinician or others via a patient management network (e.g., the CareLink network owned by Medtronic, Inc.). The alert message can include temporal information, duration of x-ray exposure, device response, physiologic data regarding the patient, and the like.

Figure 7:
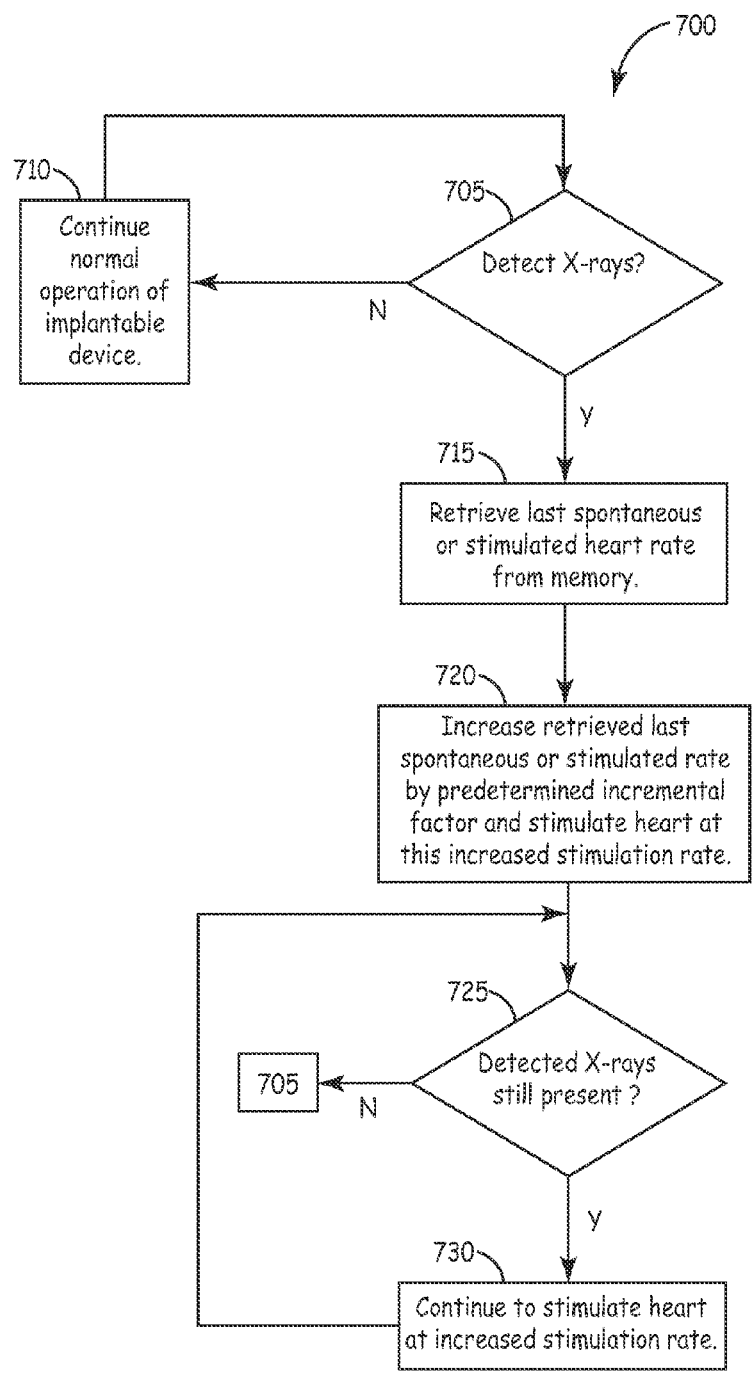
FIG. 7 illustrates a process for controlling the IMD of FIG. 1 in response to the presence of x-ray radiation interference signals according to another embodiment of the present invention.

Turning now to FIG. 7, a process 700 is illustrated for controlling the IMD 105 in response to the detection of any x-ray radiation. The process 700 commences at block 705 where the radiation detector 320 of the processor unit 120 determines if the presence of radiation exists. If the radiation does not exist (i.e., is not detected), the process 700 continues to block 710 where the implantable device 105 resumes a normal operation. If, however, the radiation is detected by detector 320, then the process 700 proceeds to block 715 where the CPU 305 recalls the last spontaneous or stimulated heart rate stored in the memory 315 prior to the detection of x-ray radiation.

At block 720, the CPU 305 then augments this recalled last heart rate (whether spontaneous or stimulated) of the implantable device 105 by a predetermined incremental factor, which may be a function of the spontaneous or stimulated heart rate retrieved from the memory 315 at block 715. The implantable device 105 then makes this augmented heart rate the new stimulation rate and stimulates the heart 112 at this new augmented stimulation rate. In accordance with the illustrated embodiment, the predetermined incremental factor may be a percentage of the stored spontaneous or stimulated rate, such as 10%, for example. It will further be appreciated that the predetermined incremental factor may be a fixed value of 10 ppm, for example, to be added to the last recalled spontaneous or stimulated heart rate.

Subsequent to increasing the stimulation rate by the predetermined incremental factor, the process 700 proceeds to block 725 where it is determined if the detected radiation still exceed the pre-selected threshold. If the pre-selected threshold is no longer exceeded, the process reverts back to block 705. If, however, the strength of the detected signals exceeds the pre-selected threshold, then the CPU 305 (at block 730) continues to stimulate the patient's heart at the new augmented stimulation rate until it is determined that the threshold is no longer exceeded.

Figure 8:
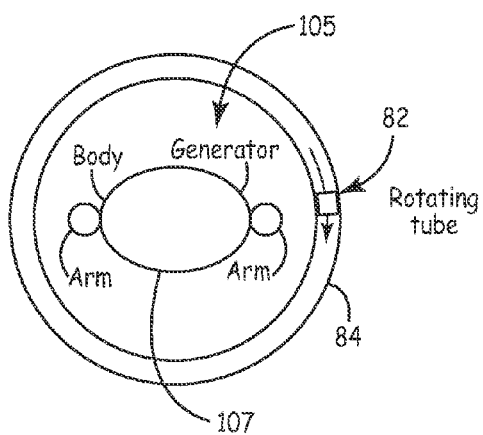
FIG. 8 is a representation of a superior cross-section of a patient with an implanted device, positioned in the CT scanner bore.

Referring now to FIG. 8, which schematically depicts an imaging unit 84 that generates x-ray exposure from an rotating imaging source 82 around a patient 107 having an implantable pulse generator (IPG) 105 implanted for physiologic monitoring and/or therapy delivery. The magnitude of the x-ray radiation impinging upon the IPG 105 depends in large part upon the incident angle of the radiation (see FIG. 9), the materials used to fabricate the implantable device, body tissue effects (e.g., attenuation) and relative placement of the patient and the device within the bore the imaging device 84 (e.g., a CT scanner). As the x-ray tube 82 rotates over time, the maximum effect occurs when the radiation is tangent to the surface of the device, and the least effect occurs on the opposite side of the body 107, where tissue attenuation and distance become a major factor in the x-ray intensity presented to an IMD.

Figure 9:
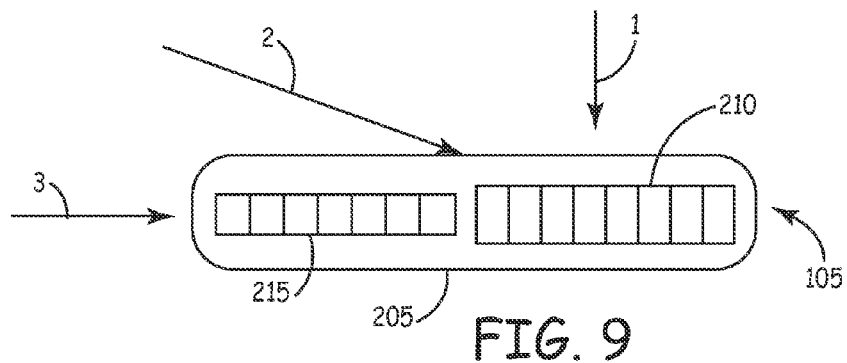
FIG. 9 represents a cross-section of a device and different x-ray angles, and illustrates how device materials and components may contribute to the attenuation of the x-ray intensity.
Figure 10:
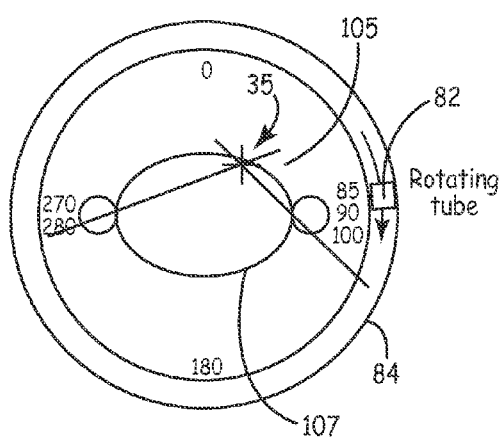
FIG. 10 illustrates several different incident angles for a rotating x-ray imaging scanner.
Figure 11:
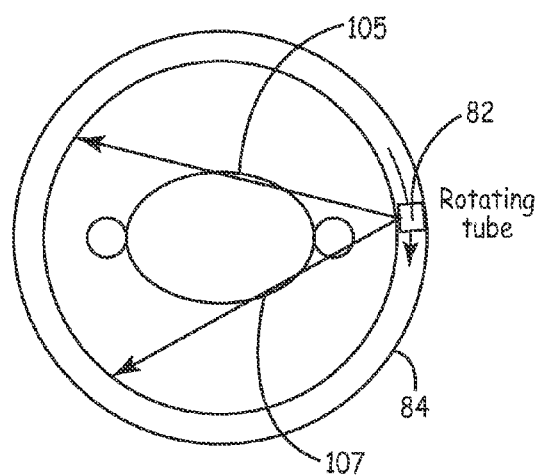
FIG. 11 illustrates that under certain circumstances a rotating x-ray imaging scanner might not image an implanted medical device (IMD).

Depending on the incident angle, the device will be subjected to varying levels of x-ray intensity as depicted in FIG. 9 showing a cross-section of a device 105 and different x-ray angles (denoted by arrows numbered 1,2,3), and illustrates how device materials and internal components (210,215) may contribute to the attenuation of the x-ray intensity. The metallic titanium or steel case of an IMD is typically relatively thin, so any x-ray directly over the device (arrow number 1) has little attenuation. As the x-ray source 82 moves around the device (arrow 2), the x-ray attenuation increases, but will pass quickly, approximately in a millisecond. In addition, the internal electronics 210,215 may transiently shadow a device's components (3) as the beam rotates around the gantry 84. Another factor is the device orientation in the bore of the CT scanner as depicted schematically at FIG. 10 which illustrates that when the x-ray tube 82 is about 35 degrees relative to the device 105, the device 105 is closer to the source than when the beam is at about 215 degrees. Radiation intensity varies inversely (by the square of the radius), so small changes in distance make significant changes in radiation intensity. The radiation intensity declines about half for every 4 cm of tissue penetrated (@100 kV). When the tube 82 is directly over the device 105 there is almost no attenuation, but when the tube 82 is below the patient 107, the radiation reaching the device declines to about 6% of what is entering the patient's back. Given that device 105 is typically implanted off-center, especially in the case of a cardiac pacemaker (e.g., either in the right or left pectoral region of the patient 107), FIG. 11 shows that there is also a possibility that the device 105 could be out of the x-ray beam for a few milliseconds for each rotation of the x-ray tube 82. Any combination of attenuation factors combined with the rotation of the x-ray tube 82 can result in modulated x-ray intensity to the device 105. Given the different rotational tube speed settings (0.3 to 1.5 rotations/second) of many types of CT scanners, the frequency of modulated x-ray intensity would either increase or decrease. At high enough x-ray intensities, this effect could contribute to device instability due to the interaction between the x-rays and circuitry operatively coupled within the IMD 105.

EXAMPLE

Fluoroscopy

An x-ray source was directed from underneath an IMD 105 to expose the hard die coat side of the hybrid circuitry. The tube settings were 120 KV & 0.4 mA and the ECC sensor output was approximately 1 mV when the fluoroscope was turned on. No device interaction was observed, whether the fluoroscopy was turned "on" or "off".

EXAMPLE

Standard X-Ray

For this testing, the x-ray source was directed from the topside of a table, so it impinged upon the flip-chip side of the hybrid first. The microprocessor and sense amplifier chips are mounted on the flip-chip side of the hybrid, so the radiation penetrated from the backside of the die. The tube settings ranged from 120 KV & 143 mA for a 1 sec (143 mAs) exposure to 120 KV & 49 mA for the 16 sec (778 mAs) exposure. The response observed at the sense amplifier was an AC-coupled high-pass waveform. The voltage gain to the sense amplifier was approximately 1000. The most likely cause of the large transient voltage is a shift in the offset voltage of one of the previous stages in the sense amplifier. A shift of 8 mV was seen in the voltage reference, and it is assumed that a similar shift is occurring somewhere in the sense amplifier. The sensor output was 120 mV for the 120 KV/143 mA/1 sec exposure setting. The IB50 test output was monitored during the exposure by running a 50 nA output into the 1 Mohm input of an oscilloscope resulting in a 50 mV DC level. No shift was observed; however, there was a significant amount of 60-cycle noise present, so a high-resolution measurement was not possible.

Figure 12:
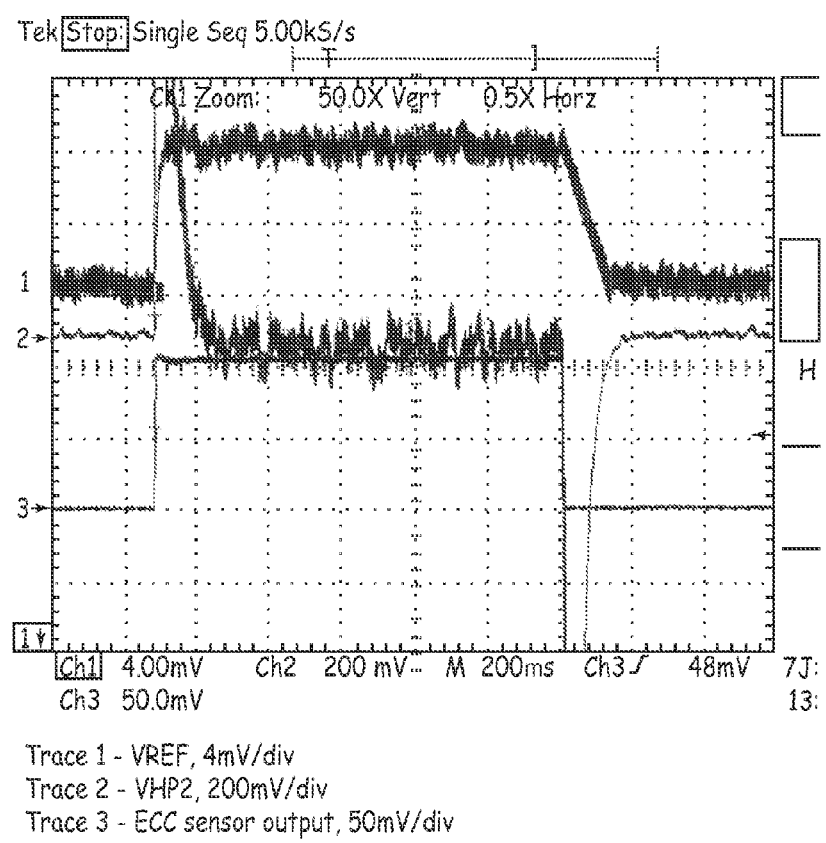
FIGS. 12-14 graphically represent several output signals during x-ray radiation exposure.

FIG. 12 shows the output from an ECC sensor, VREF and VHP2 for a 1.1 second exposure. During this exposure, the ECC sensor measured 105 mV and VREF shifted 8 mV positive. The VHP2 had a large response to both the lead and trailing edge of the exposure. The output saturated, so the signal was at least 10× the detect level and ROUT detect pulses were generated on both of the edges. The sense amplifier noise during the exposure time was higher than the quiescent noise level; however, it was not high enough to generate any detect pulses.

Figure 13:
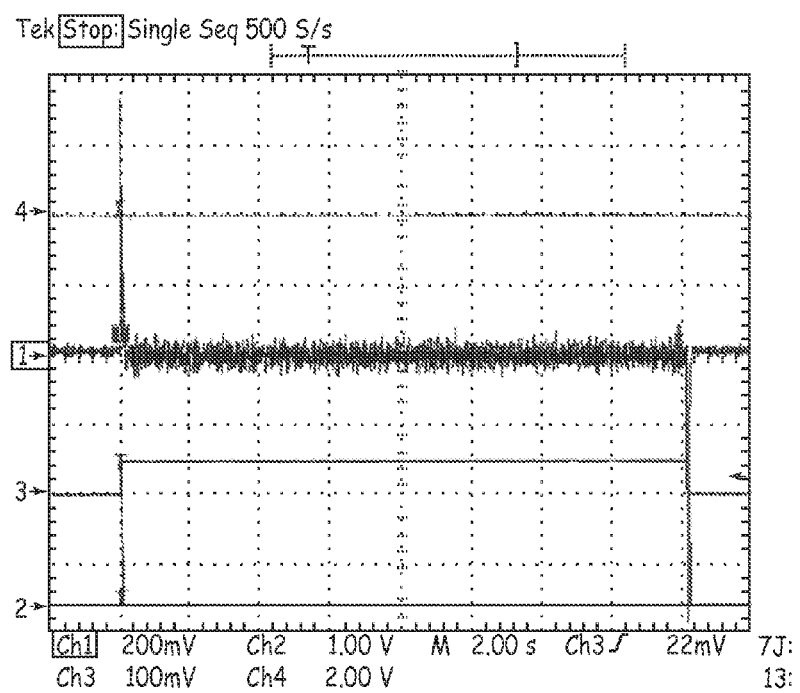

FIG. 13 shows the output of the ECC sensor, VHP2 and ROUT for a 16 second exposure. During this exposure the tube current was reduced and the ECC sensor measured 50 mV. A large response was generated at VHP2 at the lead and trailing edge of the exposure and ROUT detect pulses were generated on both of the edges.

Figure 14:
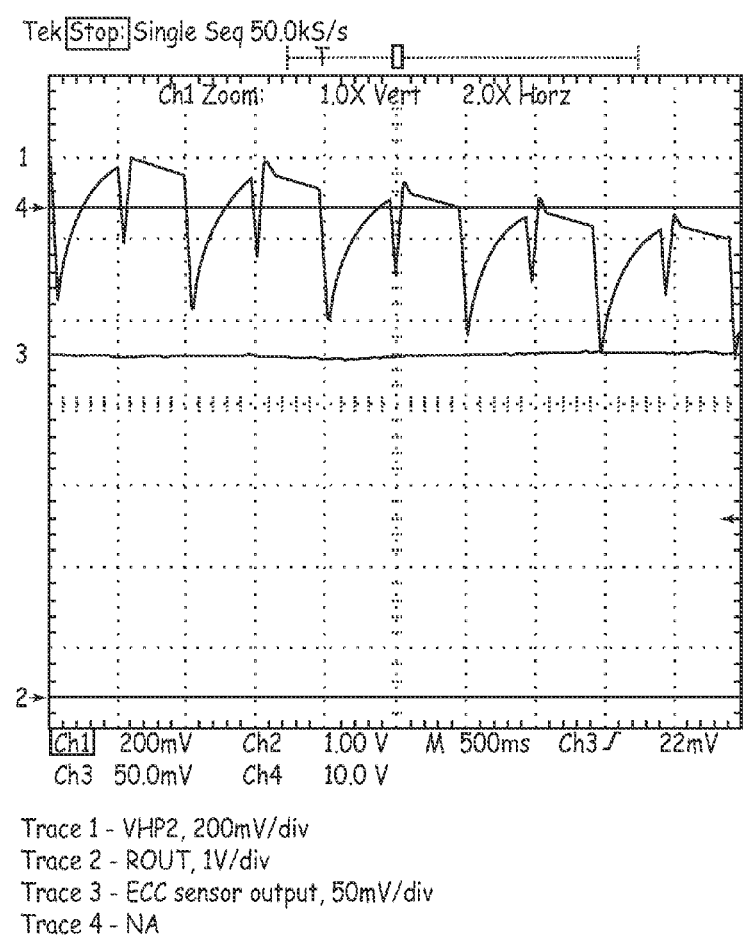

FIG. 14 shows the output of the ECC sensor, VHP2 and ROUT during a high level exposure; the x-ray sensor measured 128 mV. The figure zooms in on the transient recovery of the VHP2 following the leading edge of the exposure. The waveform has a large component at the 1024 Hz sampling clock frequency during the recovery period.

A large response in the sense amplifier was observed at the leading and trailing edges of the x-ray exposure; this response was at least 10× the detect level and sensed events were generated on both edges. A shift in the VREF occurred during the entire exposure period of the x-ray. Placing a piece of lead over the L266 sense amplifier chip eliminated the sense amplifier response due to the x-ray exposure. If the x-ray exposure generated from a CT scanner is duty-cycled on/off (or modulated by tissue attenuation as the beam rotates around the body), a sensed event on every transition could result in numerous partial or complete oversensing during each revolution. Even with a constant radiation dose rate during the scan, the effect on the sense amplifier IC wouldn't be constant during the scan as changes in the incident angle and other coupling mechanisms could modulate any offset voltages that are generated. When a small piece of lead was place over the L266, the VHP2 did not respond to the x-ray exposure. We did not place a titanium shield half over the hybrid to determine the amount of attenuation that the can would provide in an actual device.

This testing validates the theory that photocurrents of sufficient magnitude are generated in the silicon during x-ray exposure and at high enough levels affect normal operation of sensitive circuits. Diverse shapes and locations of the lead plate shield over the hybrids were tested. Through movement of the lead shielding, the area of x-ray interaction was verified and it corresponded with the crystal oscillator clock monitor circuitry.

Figure 15:
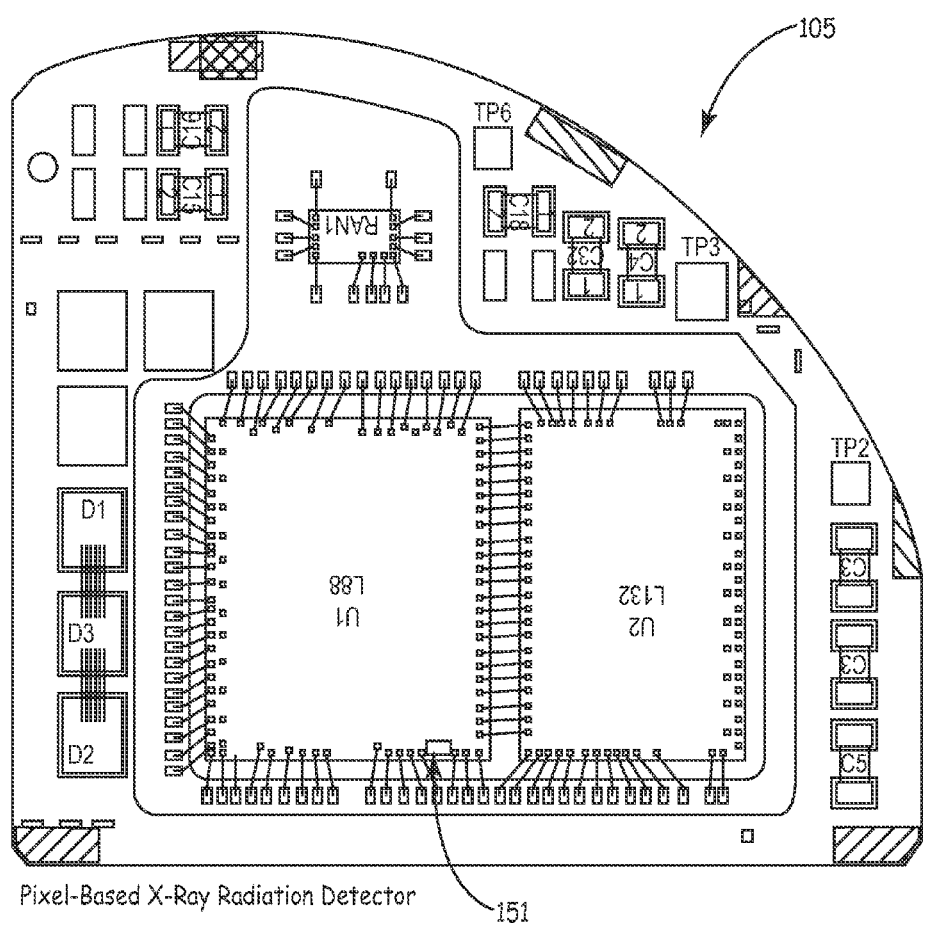
FIG. 15 is a plan view of a portion of circuitry for operating an IMD with a pixel-based x-ray radiation detector schematically depicted.

FIG. 15 is a plan view of a portion of circuitry for operating an IMD 105 with a pixel-based x-ray radiation detector 151 schematically depicted. The detector 151 can comprise a charge coupled device (CCD) having one or more pixel units and the CCD can include programmable threshold level(s). However, in one embodiment of the invention the mere presence of any radiation within the hermetically sealed IMD housing triggers remedial action, wireless notification or alert or a mode-switch of the operating parameters of the IMD.

Figure 16:
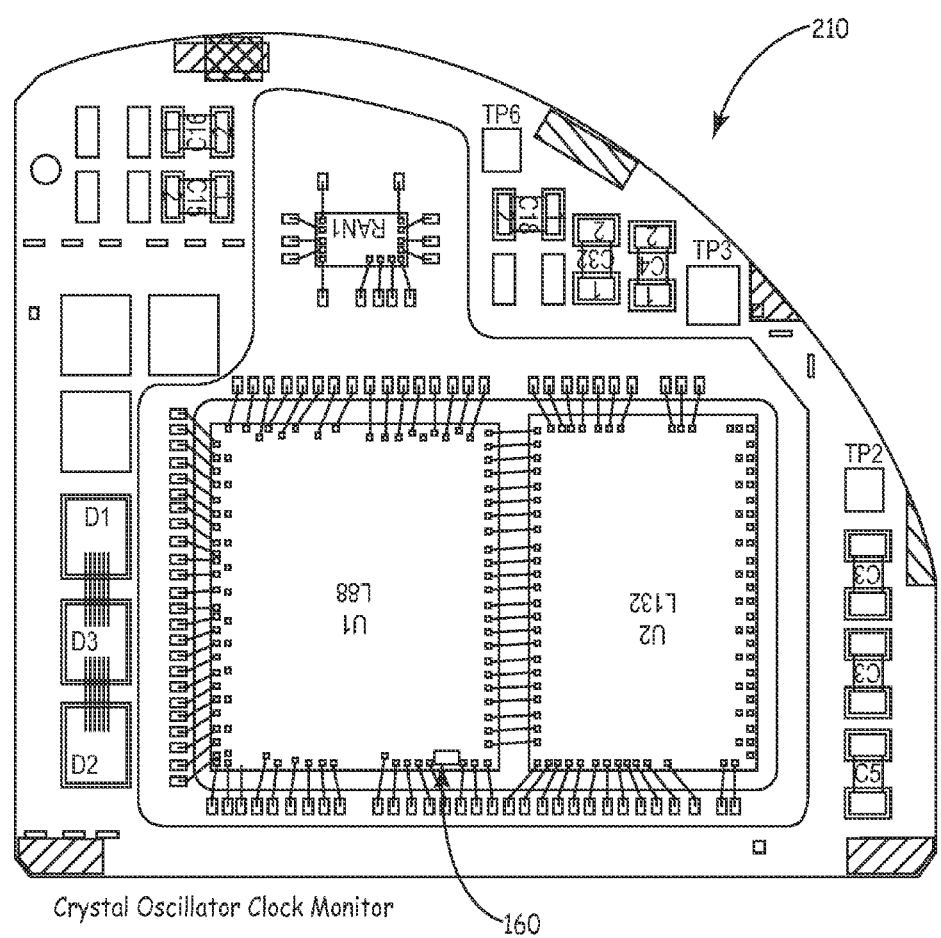
FIG. 16 is a plan view of a portion of circuitry for operating an IMD with a crystal oscillator clock monitor circuit schematically depicted.

FIG. 16 is a plan view of a portion of circuitry for operating IMD 210 circuitry with a crystal oscillator clock monitor circuit 160 schematically depicted. Since we herein described the most vulnerable portion of the circuitry was the clock monitor circuit, this circuit needs to be shielded and/or switched-out of operation in the event that x-ray radiation is detected within the IMD housing.

Figure 17:
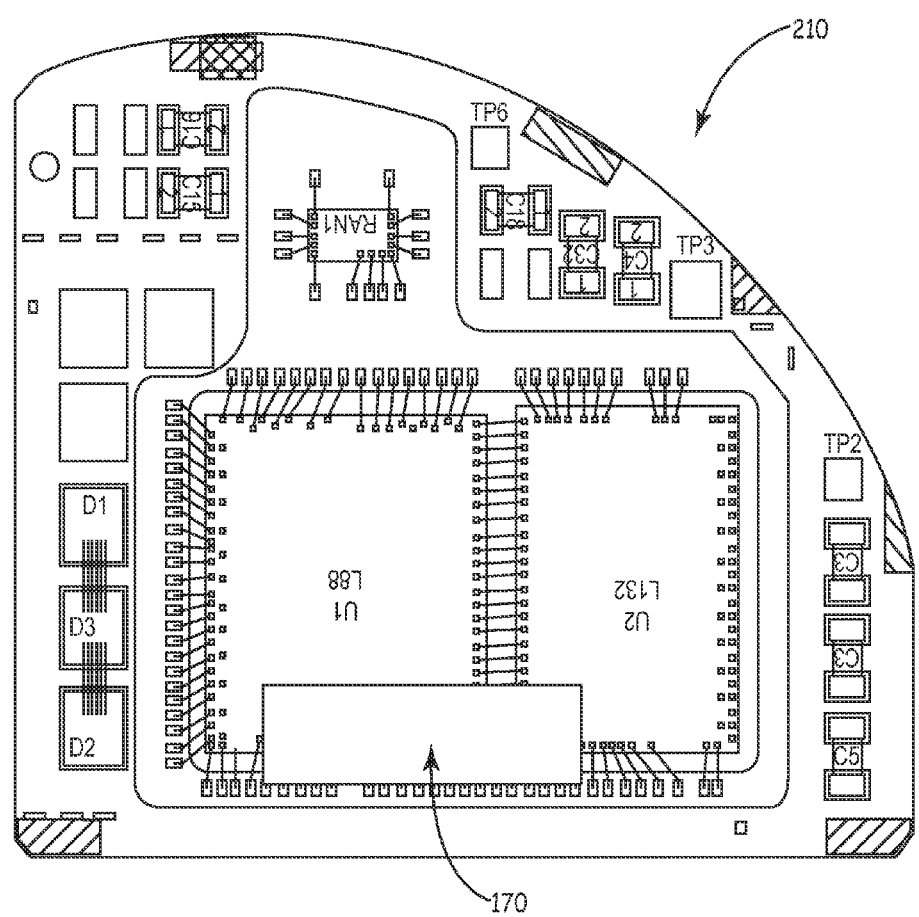
FIG. 17 is a plan view of a portion of circuitry for operating an IMD with a plate of radiation opaque materially strategically located over a potentially vulnerable portion of the circuitry.

FIG. 17 is a plan view of a portion of circuitry 210 for operating an IMD with a plate of radiation opaque material 170 strategically located over a potentially vulnerable portion of the circuitry 210. Although a geometric portion of radiation opaque material is depicted in FIG. 17, non-geometric and/or irregularly shaped materials can be used. In one embodiment, a plate of lead is used to shield the circuitry although other materials can be used. In addition, the plate of material can be covered on at least one major surface with a dielectric material (e.g., a layer of oxide, a coating of medical grade adhesive, etc.). Also, although a substantially planar portion of material 160 is depicted a three-dimensional (3D) structure can be implemented according to the invention.

The inventors thus verified the mechanism of interaction generated by the photoelectric effect induced during exposure to x-ray radiation. Subsequent laboratory testing confirmed that x-ray generated photocurrents most likely affect the sense amplifier circuitry used to sense cardiac activity. Interaction resulted in oversensing of cardiac activity and partial electrical reset (PER) for some of the tested units and just oversensing with the tested ICD.

Additionally, extensive testing was conducted to look for other events that could be caused by a CT scan, and none were found, with the exception of oversensing. Lead shielding was used to isolate portions of the circuitry from the x-ray beam. This series of tests clearly demonstrated the root cause is associated with x-ray radiation, and not a result of any other electric or magnetic interference. The inventors suggest that the mechanism for the PER is the result of photocurrents caused by high levels of x-ray radiation interacting with the clock monitor circuitry for the crystal oscillator circuit (used to generate the main clock for the pacemaker). When the clock monitoring circuit detects what it perceives as anomalous operation of the clock, then the clock monitor circuit will activate a startup mode, and a PER is generated.

Testing was conducted at worst-case conditions as the device was in air with no form of simulated human tissue. To reflect a more conservative approach to the test procedure a human body phantom, which would attenuate the effect, was not used.

The inventors thus confirmed that intermittent oversensing and PER events occur when an IMD is exposed to higher levels of x-ray radiation (e.g., generated by a 16-slice CT scan equipment when the device electronics are directly under the beam).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

For example, a portion of x-ray opaque material can comprise a portion of the shield for an IMD such as a relatively thicker region of titanium for a titanium encased IMD. Alternatively, the x-ray opaque material can comprise a layer of material deposited directly upon a portion of a substrate that carries the vulnerable component or circuitry and/or upon a portion of packaging for said vulnerable component or circuitry. Also, in response to an affirmative detection of x-ray radiation within an IMD one or more of the following remedial steps can be performed: increasing bias currents within the operative IMD circuitry altering operating points of sensitive circuits.

The invention claimed is:

1. An implantable medical device (IMD), comprising:
    a substantially hermetic housing;
    processing means for operating and controlling the IMD disposed at least partially within the housing, said processing means including circuitry vulnerable to damage by imaging X-ray radiation;
    a portion of material opaque to imaging X-ray radiation disposed within the housing and intermediate the circuitry and the housing, said material configured to cover only part of the processing means, the part of the processing means covered including the x-ray vulnerable circuitry.

2. A device according to claim 1, wherein the processing means is further adapted to adjust a stimulation rate in which the IMD stimulates a heart.

3. A device according to claim 1, wherein the IMD comprises a pacemaker.

4. A device according to claim 1, wherein the portion of x-ray opaque material comprises a substantially planar sheet of material.

5. A device according to claim 4, wherein the material comprises one of a ceramic material and a metallic material.

6. A device according to claim 1, wherein the material comprises lead.

7. A device according to claim 1, wherein the IMD comprises an implantable cardioverter-defibrillator.

8. A device according to claim 1, wherein the IMD comprises a nerve stimulator.

9. A device according to claim 1, wherein the IMD comprises a drug pump.

10. A device according to claim 1, wherein the IMD comprises an implantable pulse generator.

11. A device according to claim 1, wherein the IMD comprises an implantable brain stimulator.

12. An implantable medical device (IMD), comprising:
a substantially hermetic housing;
processing means for operating and controlling the IMD disposed at least partially within the housing, said processing means including circuitry vulnerable to damage by imaging X-ray radiation;
a portion of material opaque to imaging X-ray radiation disposed within the housing and intermediate the circuitry and the housing, said material configured to cover a part of the processing means including the x-ray vulnerable circuitry.

13. A device according to claim 12, wherein the portion of x-ray opaque material comprises a substantially planar sheet of material.

14. A device according to claim 12, wherein the material comprises one of a ceramic material and a metallic material.

15. A device according to claim 12, wherein the material comprises lead.

16. A device according to claim 15, wherein the processing means is further adapted to adjust a stimulation rate in which the IMD stimulates a heart.

17. A device according to claim 15, wherein the IMD comprises a pacemaker.

18. A device according to claim 15, wherein the IMD comprises an implantable pulse generator.

19. A device according to claim 15, wherein the IMD comprises a drug pump.

* * * * *